US011332516B2

(12) United States Patent
Renault et al.

(10) Patent No.: US 11,332,516 B2
(45) Date of Patent: May 17, 2022

(54) ANTIBODY PURIFICATION METHOD

(71) Applicant: QBD (QS-IP) LIMITED, St Helier (GB)

(72) Inventors: Neil Renault, Midlothian (GB); Andrew Gordon Robb, Midlothian (GB); Janine Scott Robb, Newbridge (GB); David Cooper Robson, Midlothian (GB)

(73) Assignee: QBD (QS-IP) LIMITED, St Helier (JE)

( * ) Notice: Subject to any disclaimer, the term of this patent is extended or adjusted under 35 U.S.C. 154(b) by 364 days.

(21) Appl. No.: 15/779,391

(22) PCT Filed: Nov. 25, 2016

(86) PCT No.: PCT/GB2016/053721
§ 371 (c)(1),
(2) Date: May 25, 2018

(87) PCT Pub. No.: WO2017/089827
PCT Pub. Date: Jun. 1, 2017

(65) Prior Publication Data
US 2018/0305442 A1 Oct. 25, 2018

(30) Foreign Application Priority Data
Nov. 26, 2015 (GB) ................................. 1520903.4

(51) Int. Cl.
*C07K 16/06* (2006.01)
*C07K 16/34* (2006.01)

(52) U.S. Cl.
CPC ............ *C07K 16/065* (2013.01); *C07K 16/34* (2013.01); *C07K 2317/21* (2013.01)

(58) Field of Classification Search
None
See application file for complete search history.

(56) References Cited

U.S. PATENT DOCUMENTS

| 3,903,254 | A | | 9/1975 | Dahlgren et al. | |
|---|---|---|---|---|---|
| 5,977,306 | A | * | 11/1999 | Grieve | G01N 33/5308 530/350 |
| 2006/0211035 | A1 | * | 9/2006 | Itescu | G01N 33/56977 435/6.14 |
| 2010/0150942 | A1 | | 6/2010 | Cantor | |
| 2010/0256005 | A1 | * | 10/2010 | Petri | G01N 33/54393 506/9 |
| 2013/0280275 | A1 | * | 10/2013 | Liu | C07K 16/2878 424/173.1 |

FOREIGN PATENT DOCUMENTS

| CA | 1144858 | | 4/1983 | |
|---|---|---|---|---|
| EP | 0223978 | | 6/1987 | |
| EP | 0223978 | A1 * | 6/1987 | ........... G01N 33/532 |
| EP | 0680316 | B1 | 12/2003 | |
| EP | 2933268 | B1 | 7/2017 | |
| GB | 1377102 | | 12/1974 | |
| JP | S6288963 | A | 4/1987 | |
| JP | H08505772 | A | 6/1996 | |
| JP | 2011239784 | A | 12/2011 | |
| JP | 2013538057 | A | 10/2013 | |
| WO | 93/18398 | | 9/1993 | |
| WO | 2011/139389 | | 11/2011 | |

OTHER PUBLICATIONS

Jenkins et al., Transfusion, 1977, 17(2):110-114. (Year: 1977).*
Judd, Transfusion Medicine Reviews, 1999, 13(4): 297-310. (Year: 1999).*
Caruccio, L. et al: "A novel method using formamide for the elution of antibodies from erythrocytes," VOX SANGUIS, 83(1)63-69 (2002).
International Search Report and Written Opinion regarding International Application No. PCT/GB2016/053721, dated Feb. 8, 2017, 15 pages.
Judd, W. John, "Elution-Dissociation of antibody from red blood cells: Theoretical and practical considerations," Transfusuin Medicine Reviews, 13(4):297-310 (1999).
Jenkins. Jr., D.E. et al. "A rapid method for the preparation of high potency auto antibody and alloantibody eluates," Transfusuin (Bethesda), 17(2):110-114 (1977).
Great Britain Search Report corresponding to GB1520903.4; dated Jul. 26, 2016 (5 pp).
Siegel et al. "Expression and Characterization of Recombinant Anti-Rh(D) Antibodies on Filamentous Phage: A Model System for Isolating Human Red Blood Cell Antibodies by Repertoire Cloning" Blood, 83(8): 2334-2344 (1994).
Japanese Office Action corresponding to JP 2018-546772; dated Nov. 9, 2020 (8 pages, including English translation).
European Office Action corresponding to EP 16805206.6; dated Jul. 30, 2019 (7 pages).
Wang, Hui , et al., "Lack of CD47 on nonhematopoietic cells induces split macrophage tolerance to CD47null cells", PNAS 104(34), 2007, 13744-13749.

* cited by examiner

*Primary Examiner* — Nicole Kinsey White
(74) *Attorney, Agent, or Firm* — Myers Bigel, P.A.

(57) ABSTRACT

Disclosed are methods by which compounds/molecules capable of binding antigens, for example antibody type compounds/molecules, can be purified, extracted and/or selected. The methods may be used to purify, extract or select a specific type (or types) of binding agent from a mixed composition. The methods may be used to extract or purify specific binding agents from mixed compositions, which compositions comprise other agents capable of binding other antigens. The methods may find particular application as methods for the purification of blood group antigen antibodies.

11 Claims, 16 Drawing Sheets

Sourceplate Schematic

Figure 3:
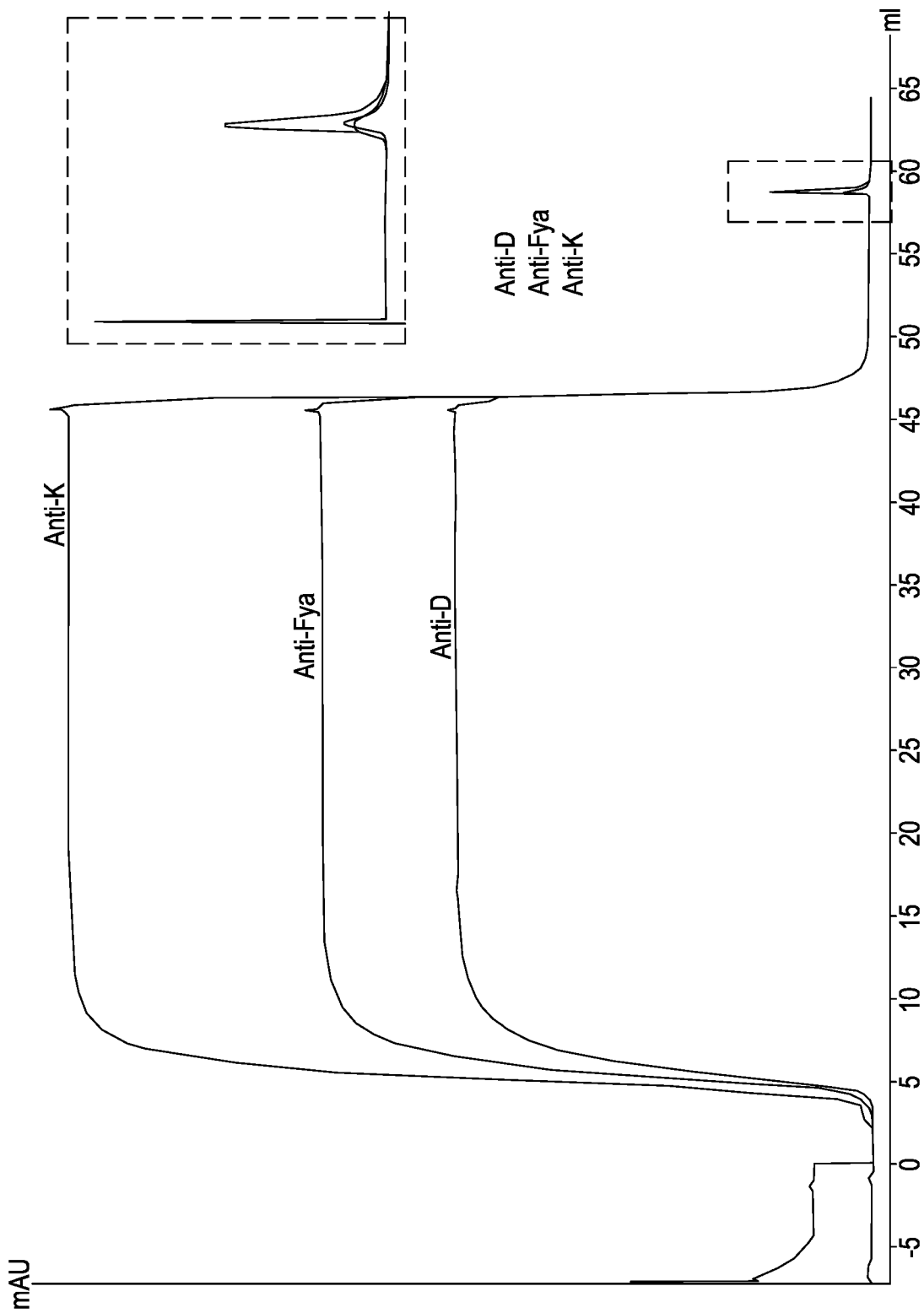

| 6 | 26 | Anti-D Post Protein G 1/8 | 32 | MS56 B01Pent conc 1/32 |
|---|---|---|---|---|
| 5 | 2 | Anti-D Post Protein G 1/32 | 8 | MS56 B01Pent conc 1/128 |
| 4 | 30 | Anti-K Post Protein G 1/8 | 36 | Anti-Glycophorin 1/40 |
| 3 | 6 | Anti-K Post Protein G 1/32 | 12 | DG-FYA-02 Mono Conc 1/4 |
| 2 | 34 | Anti-Fya AC CONC 1/8 | 29 | ESD1 Mono 1/40 |
| 1 | 10 | Anti-Fya AC CONC 1/32 | 4 | ESD1 Mono 1/160 |
|   | A | B | C | D |

Figure 1

| Anti-Fya AC CONC 1/16 | 45 | ESD1 Mono 1/80 | 39 |
| --- | --- | --- | --- |
| Anti-Fya AC CONC 1/64 | 21 | ESD1 Mono 1/320 | 15 |
| Anti-D Post Protein G 1/16 | 37 | MS56 B01 Pent conc 1/64 | 43 |
| Anti-D Post Protein G 1/64 | 13 | MS56 B01 Pent conc 1/256 | 19 |
| Anti-K Post Protein G 1/16 | 41 | DG-FYA-02 Mono Conc 1/2 | 47 |
| Anti-K Post Protein G 1/64 | 17 | DG-FYA-02 Mono Conc 1/6 | 23 |
| E | F | G | H |

Figure 1 cont.

| 0 | 0 | 0 | 0 |
|---|---|---|---|
| 50 | Anti-D Post Protein G 1/2 | 56 | MS56 B01Pent conc 1/8 |
| 0 | 0 | 0 | 0 |
| 54 | Anti-K Post Protein G 1/16 | 60 | Anti-Glycophorin 1/10 |
| 0 | 0 | 0 | 0 |
| 58 | Anti-Fya AC CONC 1/2 | 52 | ESD1 Mono 1/10 |
| I | J | K | L |

Figure 1 cont.

| 0 | 0 | 0 | 0 |
|---|---|---|---|
| Anti-Fya AC CONC 1/4 | 69 | ESD1 Mono 1/20 | 63 |
| 0 | 0 | 0 | 0 |
| Anti-D Post Protein G 1/4 | 61 | MS56 B01 Pent conc 1/16 | 67 |
| 0 | 0 | 0 | 0 |
| Anti-K Post Protein G 1/4 | 65 | Anti-Glycophorin 1/20 | 71 |
| M | N | O | P |

Figure 1 cont.

| | 1 | 2 | 3 | 4 | 5 | 6 |
|---|---|---|---|---|---|---|
| 1 | Anti-D Post Protein G 1/64 | 2 | ESD1 Mono 1/320 | 4 | | 6 |
| 2 | Anti-D Post Protein G 1/64 | 2 | ESD1 Mono 1/320 | 4 | Anti-K Post Protein G 1/64 | 6 |
| 3 | 13 | Anti-D Post Protein G 1/32 | 15 | ESD1 Mono 1/160 | Anti-K Post Protein G 1/64 | 6 |
| 4 | 13 | Anti-D Post Protein G 1/32 | 15 | ESD1 Mono 1/160 | 17 | Anti-K Post Protein G 1/32 |
| 5 | Anti-D Post Protein G 1/16 | 26 | ESD1 Mono 1/80 | 29 | 17 | Anti-K Post Protein G 1/32 |
| 6 | Anti-D Post Protein G 1/16 | 26 | ESD1 Mono 1/80 | 29 | Anti-K Post Protein G 1/16 | 30 |
| 7 | 37 | Anti-D Post Protein G 1/8 | 39 | ESD1 Mono 1/40 | Anti-K Post Protein G 1/64 | 30 |
| 8 | 37 | Anti-D Post Protein G 1/8 | 39 | ESD1 Mono 1/40 | 41 | Anti-K Post Protein G 1/8 |
| 9 | Anti-D Post Protein G 1/4 | 50 | ESD1 Mono 1/20 | 52 | 41 | Anti-K Post Protein G 1/8 |
| 10 | Anti-D Post Protein G 1/4 | 50 | ESD1 Mono 1/20 | 52 | Anti-K Post Protein G 1/4 | 54 |
| 11 | 61 | Anti-D Post Protein G 1/12 | 63 | ESD1 Mono 1/10 | Anti-K Post Protein G 1/4 | 54 |
| 12 | 61 | Anti-D Post Protein G 1/12 | 63 | ESD1 Mono 1/10 | 65 | Anti-K Post Protein G 1/2 |

Figure 2

| 7 | 8 | 9 | 10 | 11 | 12 |
|---|---|---|---|---|---|
| MS56 B01 Pent conc 1/256 | 8 | Anti-Fya AC CONC 1/64 | 10 | DG-FYA-02 Mono Conc 1/8 | 12 |
| MS56 B01 Pent conc 1/256 | 8 | Anti-Fya AC CONC 1/64 | 10 | DG-FYA-02 Mono Conc 1/8 | 12 |
| 19 | MS56 B01 Pent conc 1/128 | 21 | Anti-Fya AC CONC 1/32 | 23 | DG-FYA-02 Mono Conc 1/4 |
| 19 | MS56 B01 Pent conc 1/128 | 21 | Anti-Fya AC CONC 1/32 | 23 | DG-FYA-02 Mono Conc 1/4 |
| MS56 B01 Pent conc 1/64 | 32 | Anti-Fya AC CONC 1/16 | 34 | DG-FYA-02 Mono Conc 1/2 | 36 |
| MS56 B01 Pent conc 1/64 | 32 | Anti-Fya AC CONC 1/16 | 34 | DG-FYA-02 Mono Conc 1/2 | 36 |
| 43 | MS56 B01 Pent conc 1/32 | 45 | Anti-Fya AC CONC 1/8 | 47 | Anti-Glycophorin 1/40 |
| 43 | MS56 B01 Pent conc 1/32 | 45 | Anti-Fya AC CONC 1/8 | 47 | Anti-Glycophorin 1/40 |
| MS56 B01 Pent conc 1/16 | 56 | Anti-Fya AC CONC 1/4 | 58 | Anti-Glycophorin 1/20 | 60 |
| MS56 B01 Pent conc 1/16 | 56 | Anti-Fya AC CONC 1/4 | 58 | Anti-Glycophorin 1/20 | 60 |
| 67 | MS56 B01 Pent conc 1/8 | 69 | Anti-Fya AC CONC 1/2 | 71 | Anti-Glycophorin 1/10 |
| 67 | MS56 B01 Pent conc 1/8 | 69 | Anti-Fya AC CONC 1/2 | 71 | Anti-Glycophorin 1/10 |

Figure 2 cont.

| | Slide 1 |  |
|---|---|---|
| Blank | | |
| 10 cell - Cell 1<br>O, $R_1^W R_1$ K- Fya+ Fyb+ | | |
| Blank | | |
| 10 cell - Cell 6<br>Ror K-<br>Fya- Fyb- | | |
| Blank | | |
| 3 cell - Cell 2<br>R2R2 D+ K-<br>Fya+ Fyb- | | |

Figure 5

| | Slide 2 |  |
|---|---|---|
| Blank | | |
| 10 cell - Cell 8<br>Orr K+ Fya- Fyb+ | | |
| Blank | | |
| 3 cell - Cell 3<br>Orr K+ Fya- Fyb+ | | |
| Blank | | |
| A1 rr Z401 | | |

Figure 5 cont.

ANTIBODY PURIFICATION METHOD

FIELD OF THE INVENTION

The present invention provides methods for the purification of binding agents, including, for example antibodies—in particular, human derived blood group antibodies. The methods of this invention may be applied to the purification of (polyclonal, and monoclonal) antibodies for use in pre-transfusion blood compatibility testing for the detection of blood groups on human red blood cells (erythrocytes) of donors and patient samples.

BACKGROUND OF THE INVENTION

In order to reduce non-specific binding caused by contaminating factors and to ensure concentrated amounts of antibody are present in the test system, it is routine practice to purify antibodies prior to their use in certain diagnostic systems.

For a number of blood group antigens there are no monoclonal antibody expressing cell lines available. Therefore, sourcing these rare blood group specific antibodies requires the procurement and purification of polyclonal material.

Human plasma contains many different types of proteins, including multiple IgG isoforms specific to a wide range of diverse antigens. Current monoclonal purification methods are not sufficiently focussed to enable extraction of an antibody specific to one antigen. Existing methods will adequately extract or purify all of the antibody of the same size/same structure from solution, but they will not permit the selective purification of antibodies with a specific selectivity or affinity. Purification of a polyclonal antibody with an existing monoclonal antibody purification process would result in purification of most antibody types (certainly all of the IgG antibodies) from a sample. This would result in a product containing antibodies with multiple specificities and relatively low levels of an antibody capable of binding a specific target. As such, where a quantity of specific anti-blood group antigen antibody is required, prior art monoclonal antibody purification procedures would not yield the required product.

Therefore, a procedure for the purification of binding agents (for example antibodies, including polyclonal antibodies), specific to certain antigens including blood group antigens present on red blood cells, is required. Further, in the case of antibodies with specificity/affinity for rarer blood group antigens, antibodies with the required specificity are often present within individuals producing multiple blood group antibodies; it is therefore desirable to provide methods which facilitate or permit the extraction (purification) of the specific rarer blood group antibody from the mixture.

SUMMARY OF THE INVENTION

The present invention provides methods by which compounds/molecules capable of binding antigens, for example antibody type compounds/molecules, can be purified, extracted or selected. The methods described herein may be used to purify, extract or select a specific type (or types) of binding agent from a mixed composition. For example, the methods may be used to extract or purify specific binding agents from mixed compositions, which compositions comprise other agents capable of binding other antigens.

It should be understood that while the methods of this invention may be used to purify, extract or select any type of antigen binding agent from a mix, the methods find particular application as methods for purifying, extracting or selecting antibodies. As such, for convenience, the invention will be described as relating to the purification, extraction and/or selection of "antibodies".

Further, while the methods of this invention may be used to "purify", "extract" or "select" specific antigen binding agents/antibodies from a variety of mixed compositions, for brevity these and all similar terms shall be grouped under the single terms "purify", "purification and/or "purifying". As such, the present invention will hereinafter be described with reference to "methods of purifying antibodies".

The term "specific" as applied to binding agents and/or antibodies, is intended to embrace a binding agent/antibody that binds a particular antigen (or epitope/epitopes thereof). Thus a "specific" antibody or binding agent may be an antibody or binding agent that binds a particular antigen (or an epitope or epitopes thereof). Specific binding agents/antibodies may therefore exhibit a certain selectivity, specificity and/or affinity for a particular antigen/epitope. Thus, the methods of this invention provide methods for the purification of specific antibodies—that is antibodies which bind a particular antigen or an epitope or epitopes thereof.

Similarly, the phrase "antigen specific for an antibody" refers to an antigen bound by a specific antibody. Antigens bound by specific antibodies comprise one or more epitope (s) bound by the paratope(s) of a specific antibody or antibodies.

The present invention provides adsorption based methods for the purification of antibodies.

In a first aspect, the invention provides a method of purifying antibodies said method comprising:

contacting a source of antibodies with a cell or cells expressing an antigen under conditions which permit binding between the antigen and any antibodies within the source; and isolating any bound antibody.

Antibodies purified by the methods of this invention may be specific antibodies—that is they bind a specific antigen or exhibit a selectivity, specificity and/or affinity for a particular antigen or an epitope or epitopes thereof.

As such, the antigen expressed by the cell or cells used in the methods of this invention may be specific for an antibody that is to be purified.

Thus the invention further provides a method of purifying (specific) antibodies from a source, said method comprising contacting a source of antibodies with a cell or cells expressing an antigen specific for an antibody to be purified under conditions which permit binding between the antigen and any (specific) antibodies within the source; and isolating any bound antibody.

The methods of this invention may be regarded as methods of purifying antigen specific antibodies.

One of skill will appreciate that an antigen (for example a protein and/or carbohydrate antigen) may comprise one or more epitopes. Within any given host there may be antibodies with specificity for one or more of the epitopes present on the antigen. As such, a cell for use in the methods described herein may comprise an antigen (or at least an antigenic (epitope containing) fragment thereof) to which the antibody to be purified, binds. As stated, the product of the methods of this invention is, in effect an (isolated or purified) antibody with specificity, selectivity and/or affinity for a particular antigen or epitope. The invention may be used to purify polyclonal antibodies all of which bind the same antigen but not necessarily the same epitope on that antigen.

It should be noted that the phrase "cell or cells" is used above as the methods of this invention may exploit one or more cells. Where a population of cells is used, the cells may be all of the same type with the same or similar antigen profiles. Alternatively, a population of cells for use in this invention may be a heterogeneous population comprising two or more different cell types. Where a cell population for use is heterogeneous, each cell of the population may express the same or a similar antigen profile. Alternatively, the antigen profile of the cells in the population may vary and the population as a whole may present the necessary antigen profile. For convenience, the term "cell or cells" shall be now be replaced by the term "cell"; it should be understood that the term "cell" means one or more cells (for example a population of cells). Further, the term "cell expressing an antigen" embraces not only a single cells which expresses one or more particular antigens but also two or more cells (including a population of cells) which each or collectively express one or more specific antigens. A cell for use in this invention may express and/or harbour an antigen which itself has or harbours an epitope which is bound by an antibody to be purified.

The cell or cells for use may be subject to some form of antigen blocking or neutralisation procedure or protocol. For example one or more of the antigens present on the surface of the cell may be blocked prior to the use of the cell(s) in a method of this invention. One of skill will appreciate that there are many methods available to block an antigen and these may include the use of, for example binding agents or antibodies which bind to, and thus neutralise, an antigen. The term "neutralise" should be taken to mean use of some agent which binds to an antigen and which renders that antigen (or some epitope thereof) unable to bind or interact with any other agent. Antibodies can bind to specific antigens/epitopes and such antibodies can be used to neutralise those antigens/epitopes. As such, a cell or cells for use in a method of this invention may, prior to use, be contacted or treated with a blocking agent, for example an antibody. In this way, any given cell may have one or more of the antigens it expresses selectively blocked. Additionally, or alternatively, a cell or cells for use may be treated such that one or more of the antigens expressed on the surface are rendered unable to bind an antibody. For example, the cells may be contacted with enzymes which remove epitopes or which somehow neutralise or destroy epitopes. All or part of the antigens may be cleaved form the cell surface. The reader will appreciate that in all cases, the aim will be to neutralise only those antigens which bind antibodies which are not to be purified. Those antigens which bind any antibody that the user wants to purify should be left intact so that they are free to bind antibodies. A blocking procedure or protocol may yield a "blocked cell or cells" for use. The use of a blocked cell or cells in a method described herein may increase the selectivity/sensitivity of a method of this invention and may allow the user to proceed with greater confidence that the method will yield a pure (or substantially pure) preparation of a predetermined binding agent or agents (for example some blood group specific antibody). By way of example, where a method of this invention is to be used to purify a particular blood group antigen antibody, possible contamination of the antibody preparation can be minimised (or perhaps (substantially) eliminated) by first subjecting the cell or cells to be used to a process or protocol which blocks or neutralises or destroys those antigens/epitopes which might bind antibodies which are not of interest or which should not be purified. The aim might be to almost completely neutralise the antigen profile of a cell except for that antigen (for example that blood group antigen) which binds the antibody that is to be purified.

The term "cell" or "cells" may not embrace a cell fragment, for example a cell membrane preparation or "stroma". Further, the term "cell" or "cells" may not include cells of the type described herein which are conjugated to some form of support. For example, the terms may not include a cell, cells or fragments processed therefrom (for example stroma) which are bound to or associated with some form of, for example, polymer (for example a polymer containing a benzenoid nucleus via a diazoamino bridge). The term "cell" or "cells" may not therefore embrace a cell (for example red blood cell) or membrane (for example red blood cell membrane) which is prepared as a conjugate.

The methods of this invention permit purification of a specific type of antibody or specific antibodies from any source (or sources) of the same. The methods may not be used to purge a composition (for example plasma, serum or the like) of a particular binding agent (for example an antibody). In other words the methods may not be used to remove a particular binding agent (for example an antibody) from a composition (for example plasma, serum or the like).

The source may be a mixed composition comprising more than one type of antibody as well as other proteins, compounds and molecules. For example, in addition to the antibody of interest (that is the antibody to be purified), the source may further comprise antibodies with specificity or affinity for different antigens/epitopes. As such the methods of this invention may be used to purify an antibody specific for a particular antigen from those with other antigen affinities/specificities.

The methods may be used to purify specific types of antibody from, liquid (mixed) compositions such as, for example, blood and other products derived therefrom. For example, the methods may be used to purify antibodies from plasma. Additionally, or alternatively, the methods may be used to purify antibodies from liquid compositions such as cell media. In fact, one of skill will appreciate that the methods described in this application can be applied to the purification of antibodies from a wide variety of composition types.

Where the methods of this invention exploit plasma or serum as a source from which to purify or extract an antibody with a certain specificity or affinity, the plasma or serum may be prepared from whole blood using any suitable or standard preparation protocol, or by, for example, plasmapheresis. Without wishing to be bound by any particular technique, in order to prepare plasma, whole blood may be collected and contacted with an anticoagulant. Erythrocytes and platelets may then be removed or separated by, for example, centrifugation. The resulting supernatant is designated plasma. When using plasma, an additional consideration might be the serological potency of the subject (providing the plasma or from which the plasma is obtained). One of skill will appreciate that the more of the target antibody (namely the antibody to be purified) present in the serum of the subject, the greater the antibody yield from a method of this invention. As such, with respect to any given antigen, the methods may take account of a minimum "serological potency response"—this being a measure of how much circulating antibody there is to the antigen. Subjects presenting with a serological potency response below a certain threshold might yield source material which is unlikely to contain sufficient antibody.

Plasma and/or serum for use may be derived from or provided by any suitable subject including those donating blood (blood donors), patients and/or subjects who have been immunised so as to produce antibodies to a specific target. One of skill will appreciate that using serum or plasma as a source of antibodies may yield purified polyclonal antibody preparations. It should be understood that while the invention may be used to purify human antibodies, depending on the source, the methods disclosed herein can be used to purify antibodies from other species. For example, the methods may be used to purify mammalian antibodies of all sorts (for example bovine, ovine, equine and rodent antibodies).

The term antibody may include polyclonal and/or monoclonal antibodies. Polyclonal antibodies are heterogeneous populations of antibody molecules derived from the sera of animals immunised with an antigen, or an antigenic functional derivative thereof. In order to produce polyclonal antibodies, host animals for example rabbits, sheep, pigs, etc., are immunised (perhaps by injection) with a specific antigen (wherein the antigen may optionally be supplemented with adjuvants). Monoclonal antibodies are homogeneous populations of antibodies with specificity/affinity to or for a particular antigen or epitope thereof. They can be obtained by any technique which provides for the production of antibody molecules by continuous cell lines in culture. These include, but are not limited to, the hybridoma technique of Kohler and Milstein (1975), Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Anti-bodies and Cancer Therapy, Alan R. Liss, Inc., pp. 77-96).

The method may be used to purify antibodies of any immunoglobulin class including, for example, IgG, IgM, IgE, IgA, IgD and any subclass thereof.

The methods may be used to purify naturally occurring antibodies—for example an antibody with a certain specificity or affinity generated by a subject and present in that subject's blood and plasma. The methods may be used to purify monoclonal antibodies. The methods may be used to purify antibody fragments. In such cases, the fragments will comprise an antigen binding portion. Antibody fragments may comprise Fab fragments, single chain antibodies and the like. The methods may be used to purify chimeric antibodies and/or humanised/re-surfaced antibodies. Indeed, the methods may be used to purify any type of antibody (or binding agent)—the sole requirement being that the antibody—be it an antigen/epitope binding fragment, a monoclonal, natural, polyclonal, humanised, chimeric or synthetic antibody (or the binding agent as the case might be) exhibits a specificity or affinity for the antigen expressed by the cell.

The cell may be any cell expressing an antigen to which the antibody of interest (the antibody to be purified) binds. The cell may be a naturally occurring cell and/or a cell modified to express one or more antigens. The cell may be a blood cell, for example a red blood cell (an erythrocyte). The cell may be an artificial cell, created to express one or more antigens which bind an antibody or antibodies of interest. In addition to "cells", the skilled reader will appreciate that other, perhaps synthetic, moieties may be used to affect the adsorption stage of these methods. For example substrates (including, for example beads and the like) coated with a specific antigen (for example a specific blood group antigen) may be used. Thus while the invention is described by reference to methods which exploit cells, there is potential for the methods to exploit antigen bound or immobilised to any suitable surface or substrate. In such cases, the methods of this invention may comprise the initial step of contacting a source of antibodies with an antigen under conditions which permit binding between the antigen and any antibodies within the source. The antigen may be immobilised onto a suitable surface.

Where the cell used in the methods of this invention is a red blood cell, the method may be used to purify antibodies with specificity for certain (specific) blood group antigens. The antibodies are commonly known as "blood group antibodies". Thus the methods described herein may be used to purify blood group antibodies.

As such, the invention provides a method of purifying blood group antibodies said method comprising:

contacting, under conditions which permit binding between an antigen and an antibody, a source of blood group antibodies with a cell(s) expressing a blood group antigen, wherein the blood group antigen is an antigen to which the antibody to be purified may bind; and isolating bound antibody.

The term "blood group antibody" as used herein refers to any antibody with specificity and/or affinity for a blood group antigen. A blood group antigen is one of a series of markers present on the surface of red blood cells. Most often these antigenic markers are used as a means to type blood. For example, the ABO blood typing system is based on the presence or absence of the "A" and/or "B" type antigens on the surface of red blood cells. Those red blood cells that express antigen type "A" are regarded as belonging to blood group "A". Those red blood cells expressing antigen types A and B are classed as being of type "AB". Those devoid of either the A or B antigen are classed as type "O". Additionally, red blood cells are often classed as either being Rh positive or negative—again this depends on the presence or absence of the Rh ("D") antigen—cells expressing the "D" antigen are classed as Rh positive. The term "blood group antigens" as used herein embraces any antigen (including any of those already described herein) classed as belonging to any one of the ABO, MNS, P1Pk, RH, LU, KEL, LE, FY, JK, DI, YT, XG, SC, DO, CO, LW, CH/RG, H, XK, GE, CROM, KN, IN, OK, RAPH, JMH, I, GLOB, GIL, PHAG, FORS, JR, LAN, VEL and CD59 systems. A complete list of the blood group antigen systems and types may be found at the following website (the entire contents of which is incorporated herein by reference) www.isbtweb.org/filead-min/user_upload/files-2015/red%20cells/
links%20tables%20in%20introduction%20text/
Table%20blood%20group
%20antigens%20within%20systems%20v4.0%20141124.pdf The methods of this invention may be exploited as a means to purify antibodies specific or having affinity for any type of blood group antigen, including those described herein.

It should be noted that while the invention is described with specific reference to human antibodies, the methods described herein may be applied to the purification of antibodies from other species. Indeed, no matter what the species, the principles are the same—one requires a source of the antibody to be purified (that source might be plasma from an animal) and a cell which expresses an antigen to which the antibody to be purified binds.

Antibodies (whether polyclonal or monoclonal) obtained by the methods of this invention may have a variety of applications. For example, they may have experimental, therapeutic, prophylactic and/or diagnostic utility. Those methods which use red blood cells to purify antibodies with specificity/affinity for blood group antigens may yield antibodies which find application in pre-transfusion blood compatibility testing for the detection of blood groups on human red blood cells of donors and patient samples.

Where the antibody source is (human) plasma, it must be understood that plasma contains many different types of proteins, including multiple IgG isoforms specific to a wide range of diverse antigens. Further, antibodies to some of the rarer blood group antigens are often generated by individuals producing multiple blood group antibodies. As such the methods of this invention are particularly useful as they permit the specific purification of often rare antibody types from within the complex and heterogeneous mix of proteins, antibodies and other compounds that is plasma.

Current antibody purification systems are optimised to purify monoclonal antibodies, or to extract a subclass of antibody from, for example a plasma donation. One of skill will appreciate that plasma contains antibodies to all sorts of different targets—for example plasma can contain antibodies specific to antigens present on pathogens (e.g. there may be anti-rubella, anti-influenza etc., antibodies present). Prior art purification procedures are either unsuited to polyclonal antibody purification or do not result in a product containing a specific antibody (i.e. a product comprising an antibody specific to a particular antigen); rather, the product might instead contain all antibodies of a similar type/structure present in a source.

The present invention represents an improvement over prior art monoclonal antibody purification methods as these methods are not sufficiently focussed to enable extraction of an antibody specific to one antigen; rather the prior art methods affect the purification of all antibodies having the same size/same structure. Application of an existing monoclonal antibody purification protocol to the purification of polyclonal antibodies from, for example, patient plasma would result in purification of all IgG types from the sample, resulting in a solution containing multiple antibody specificities and relatively low levels of a desired specific antibody.

A further advantage of the present invention is that it represents a rapid way of obtaining antibodies which bind to (or exhibit a specificity for) certain antigens. The methods described herein are perhaps cheaper and more convenient than any prior art method for generating monoclonal antibodies with a desired specificity. This is particularly important in the field of antibodies with specificity for red blood cell (RBC) group antigens, where not all blood group antigens (including those required to be tested by the MosaiQ™ instrument) have the corresponding antibody from expressing cell lines. Therefore purification of polyclonal antibodies is required.

As such, the methods of this invention provide antibodies for use in diagnostics, blood typing assays, blood donor/patient cross matching assays, the MosaiQ™ platform and research.

By first contacting a source of antibodies with a cell expressing a specific antigen, it is possible to extract or purify only those antibodies with specificity and/or affinity for that specific antigen. A further advantage of exploiting red blood cells (erythrocytes) in the purification of blood group antibodies is that the antigen profile of a red blood cell is effectively restricted to one which comprises blood group antigens—thus there are no other antigens which might bind unwanted antibodies. Further, it is possible to identify red blood cells with almost any combination of antigens (in other words it is possible to identify red blood cells with almost any "antigen" profile). As such, one can select one or more red blood cells which present one or more of the required antigens. In this way, through careful selection of the cell, the user can exert some control over the antibody that is to be purified. For example if antibodies with a single blood group antigen specificity are required, the user should select a red blood cell that exhibits the appropriate blood group antigen profile (preferably a red blood cell or cells which express only the antigen to which the antibody of interest binds).

As stated, the antibody source and cells are contacted under conditions which permit any antibodies in the source specific for an antigen of the cell, to bind the antigen. The conditions may be formulated so as to permit adsorption of antibodies present in the source to antigen present on the surface of the cell. Those conditions may include a period of incubation between the cells and the source. For example the cells and source may be contacted together for a predetermined time and/or at a predetermined temperature. After contact (or incubation) antibody/cell complexes may have formed—these complexes comprising antibody bound to cell surface antigen.

Any antibody/cell complexes may be separated from the source by any suitable means. For example, after contact between the cells and source, the cell/source mix may be subjected to a mechanical separation technique such as centrifugation. One of skill will appreciate that centrifugation may affect separation of any antibody/cell complexes from other components of the source including the liquid phase of the source and/or protein, carbohydrate or other components of the source which have not bound to the cell.

Where the source is a liquid source (for example plasma), after any mechanical separation step (for example centrifugation) the supernatant may be removed in a manner that does not disturb any pellet formed during centrifugation—the pellet comprising pellitised cell/antibody complexes. The pellet may be subjected to a wash procedure. For example a volume of a suitable diluent (for example saline) may be added and the pellet re-suspended and again subjected to some form of separation procedure. The wash protocol may be repeated one or more times.

In order to isolate and ultimately purify the antibodies, the bound antibodies (i.e. antibodies adsorbed to the surface of the cells) are dissociated or eluted. Any one of a number of suitable dissociation/elution procedures may be used including, for example, elution/dissociation using: heat, temperature extremes (rapid freeze/thaw), ultrasonic baths, cell lysis, reduced pH (acid elution/dissociation), cold acid, organic solvents, xylene, chloroform, modified heat (and agitation) and chloroquine diphosphate. By way of example, antibody/cell complexes (as might be present in a washed pellet) may be contacted with an elution buffer. The elution buffer may be formulated to affect antibody dissociation from cells. The elution buffer may be formulated to affect antibody dissociation through acid elution (a reduced pH). Suitable elution techniques and/or buffers will be known to one of skill in this field. For example, suitable elution techniques may be used to aid in the diagnosis of autoimmune haemolytic anaemia (AIHA), diagnosis of ABO haemolytic disease of the foetus and newborn (HDFN), identification of specificity when multiple antibodies exist in a patients serum or plasma and phenotyping red cells in patients with a positive direct antiglobulin test (DAT). Further information regarding suitable elution techniques may be found in "Elution techniques in blood bank"; 2006, Roberts, Continuing Education Topics & Issues; (see: www.americanmedtech.org/files/step online articles/ 301.pdf) the entire contents of which are incorporated by reference. An exemplary elution buffer may comprise, consist essentially of or consist of, for example, Glycine-HCl and NaCl.

After a predetermined period of time of incubation under some dissociation or elution protocol, the antibody/cell mix may be subjected to some protocol or process designed to stop or neutralise any elution or dissociation process/buffer.

After completion (and cessation/neutralisation) of the elution/dissociation step, the cell antibody mix may be subjected to some form of separation process. For example, the antibody/cell mix may be subjected to centrifugation to yield a pellet and a supernate. The supernate may contain dissociated/eluted antibodies and thus may be removed and stored.

The dissociated/eluted antibody (as might be present in a supernate) may then be subjected to a process which specifically removes, binds or immobilises antibody (for example, antibody present in the supernate). For example, the supernate may be subjected to an affinity chromatography process. Any suitable affinity chromatography process may be used and those processes suitable for antibody purification will be well known to one of skill in this field. For example, protein G columns may be used. Briefly, a preparation containing antibody (for example a supernate) may be introduced into a suitable affinity purification column and allowed to flow therethrough. After any optional washing procedures, bound antibody may be eluted from the affinity purification column and collected as an eluate. The eluate may optionally be subject to further washing, concentration and/or dialysis procedures to yield an antibody preparation for use.

Affinity based purification methods (together with subsequent concentrating and/or dialysis steps) may not only be used to yield a purified and/or concentrated antibody preparation but may also ensure that any contaminants, for example contaminants released due to cell lysis during elution, are also removed.

It should be understood that an antibody preparation prepared by the methods of this invention comprises, consists or consists essentially of antibodies having a single specificity and/or affinity—that is a specificity and/or affinity for a particular antigen. Where the method exploits a red blood cell (an erythrocyte) expressing a particular blood group antigen, antibodies yielded using the protocols of this invention may be blood group antibodies having affinity and/or specificity for that blood group antigen. Depending on the antibody source used, the antibodies may be polyclonal and/or monoclonal.

In view of the above, the invention provides a method of purifying antibodies said method comprising:

contacting a source of antibodies with a cell expressing an antigen specific for an antibody to be purified under conditions which permit binding between the antigen and antibodies within the source to form antibody/cell complexes;

dissociating antibody from the antibody/cell complexes; and purifying the dissociated antibody.

Prior to dissociating the bound antibody, any antibody/cell complexes may be separated from other components of the source by, for example centrifugation. After centrifugation the supernate may be discarded and pelleted antibody/cell complexes subjected to one or more rounds of washing.

As stated, dissociation (of antibody bound or adsorbed to the cell) may be affected through the use of some form of dissociation/elution protocol which may comprise the use of an (acidic) elution buffer.

Prior to purifying the dissociated antibody, the dissociated antibody may be separated from cell material by centrifugation. After centrifugation, the supernate may contain eluted/dissociated antibody for purification.

As stated, purification of the dissociated antibody may be achieved through the use of affinity chromatography based techniques.

Antibody purified by methods according to this invention may be characterised by, for example by any suitable qualitative/quantitative process including, for example HPLC and/or gel electrophoresis.

In a further aspect, the invention provides a kit for the purification of antibodies, said kit comprising a cell (or other entity, for example a bead or the like) comprising/expressing an antigen specific for an antibody to be purified. The kit may comprise blood cells (or other entities—for example beads of the like) comprising/expressing one or more specific blood group antigens. The kit may further comprise suitable diluents, elution/neutralisation buffers (for example acid elution buffers described herein), affinity chromatography materials and instructions for use.

The present invention will now be described in detail with reference to the following figures which show:

FIG. 1: Source plate layout for slide printing.

FIG. 2: Schematic of spot placement per mini-array.

FIG. 3: Polyclonal Anti-D and Polyclonal K Affinity Purification Run

Figure 4:
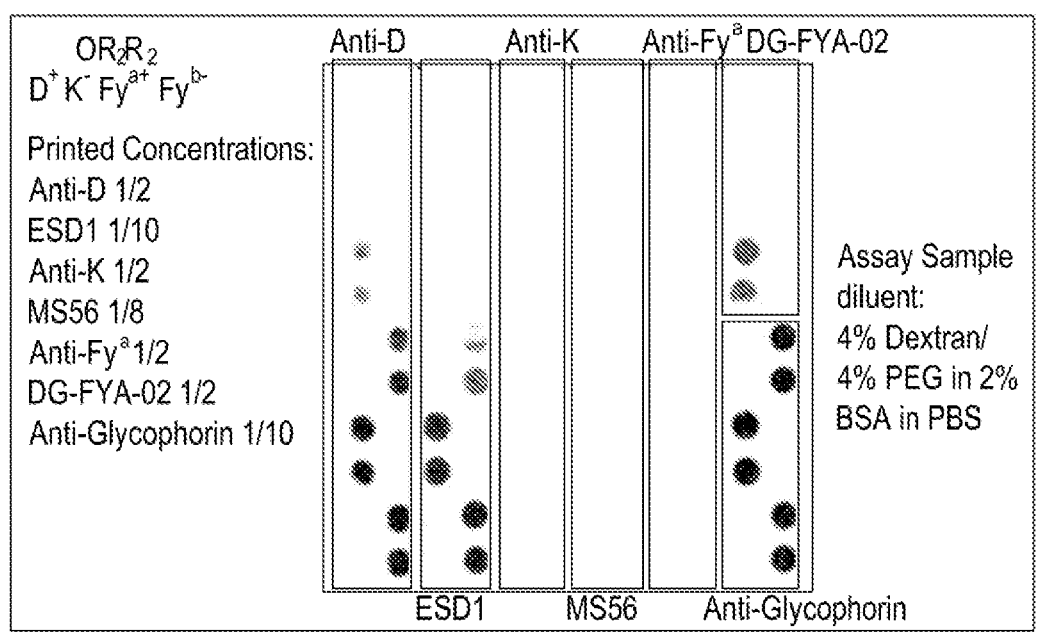
Figure 4:
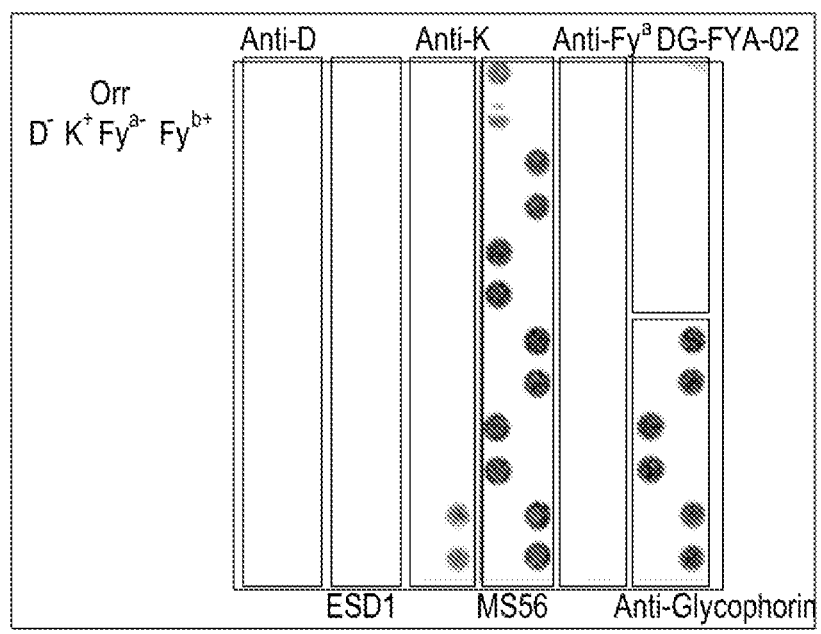
Figure 4:
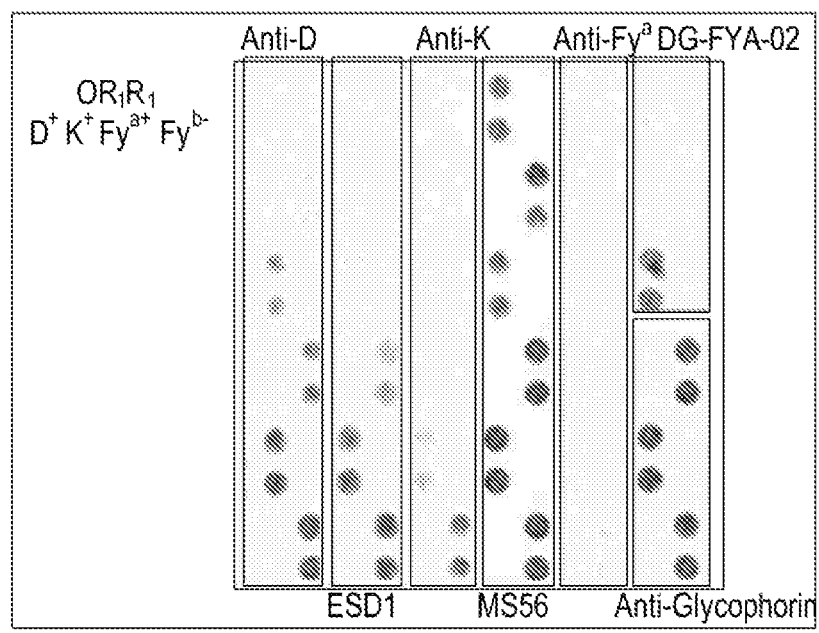
Figure 4:
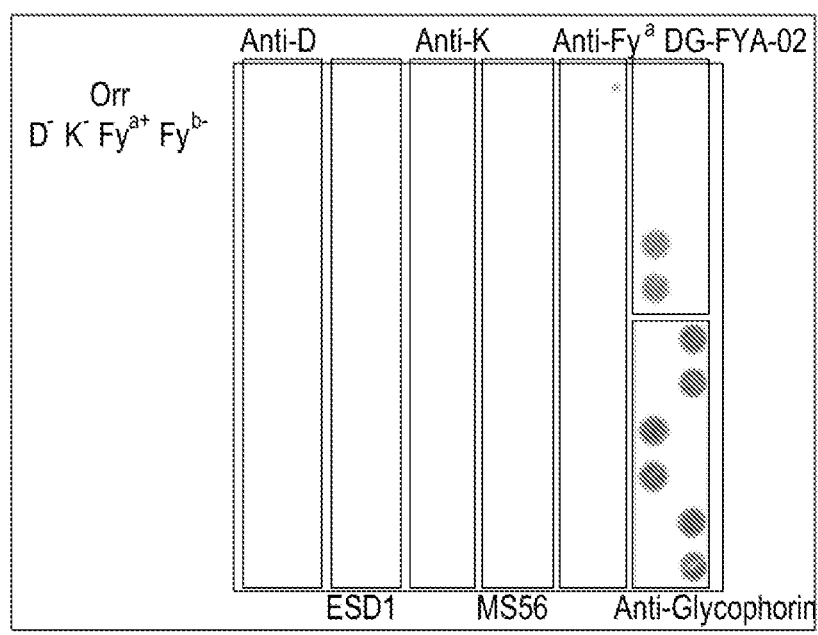

FIG. 4: Image from Assay Results, Slide 1-4 (sample diluent: 4% Dextran, 4% PEG in 2% BSA/PBS)

Figure 5:
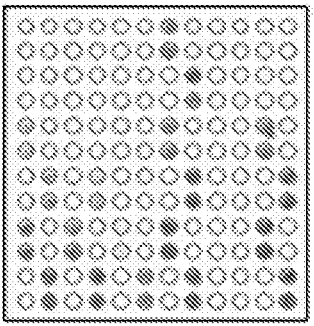
Figure 5:
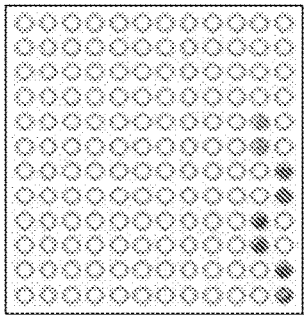

FIG. 5: Results from all wells of assay

Figure 6:
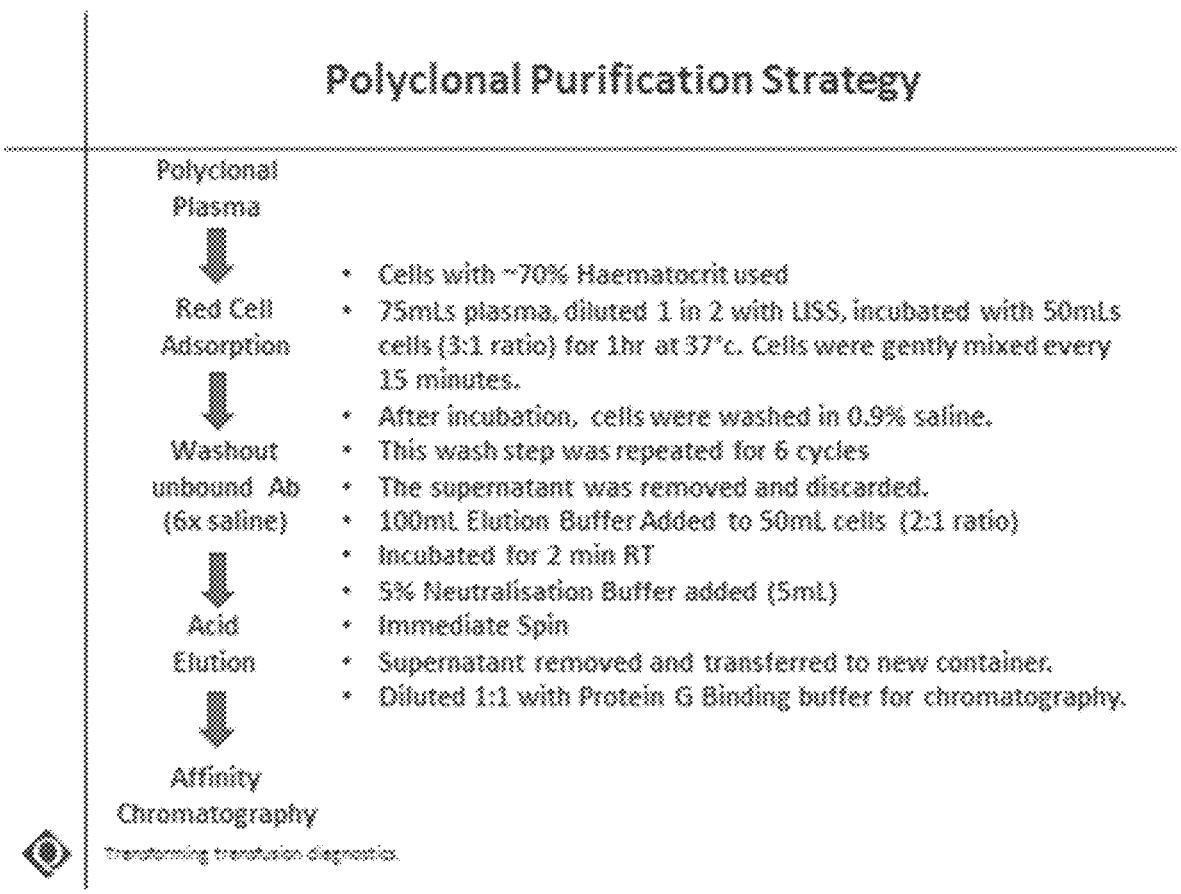

FIG. 6: An example method for the purification of polyclonal antibodies.

EXPERIMENTAL DATA

Introduction

Not all red blood cell (RBC) group antigens (including those required to be tested by the MosaiQ™ instrument) have the corresponding antibody from expressing cell lines. Therefore purification of polyclonal antibodies is required. Current methods of purification are is not sufficient since in plasma (including human plasma) there are many different antibody classes present, including multiple IgG isoforms specific to many different antigens. An efficient method for the purification of antibodies, especially blood group antibodies and in particular polyclonal antibodies, is required.

The aim of the experiment detailed in this example is to purify polyclonal antibodies from patient plasma by a method which exploits adsorption techniques, a low pH elution procedure and (IgG) affinity purification.

This large scale experiment used 25 mL of polyclonal plasma. On-slide specificity of purified fractions, utilising the current manual antigen typing assay was also evaluated.

Materials and Methods

Polyclonal Adsorption and Low pH Elution Procedure

Plasma containing Anti-D was incubated at a ratio of 2:1 (50 mL Plasma:25 mL Cells) with RhD Positive red cells at a 50% haematocrit for 1 hour at 37° C. The same procedure was carried out for plasma containing Anti-K and Anti-Fy$^a$ with corresponding red cells. It should be noted that cells at higher haematocrit, for example about 55%, about 60%, about 65%, about 70%, about 75% or about 80% may be utilised. Further alternate ratios of plasma to cells may be used. For example the ratio of plasma to cells may be about 3:1 or about 4:1. Where the haematocrit of the red blood cells is higher than about 50%, the ratio of plasma to cells may be higher than about 2:1.

After adsorption, elution of the antibodies bound to the red cells was carried out.

In order to extract haemolytic cells prior to incubation, the red cell solutions were washed six times with Saline (3000 rpm, 5 min, acceleration 9, deceleration 3.

Cells were then incubated at a volume of 2:1 (50 mL elution buffer: 25 mL cells) at room temperature for 2 minutes.

A volume (10% of cell mixture volume) of Neutralisation Buffer+154 mM% NaCl was added mixed and centrifuged at 2000×g for 60 seconds.

The supernatant was removed and transferred to a clean test tube.

The eluate was concentrated to 5 mL and diluted 1:10 in Protein G Binding Buffer in preparation for protein G affinity purification.

Acceptance Criteria:

Prior to starting red blood cells may be tested for potency and specificity.

Red cell potency criteria should react with homozygote and heterozygote cells (in other words, the cell is selected such that irrespective of the level of antigen expression (strong (homozygote) or weak (heterozygote)), it is still capable of binding antibodies)

Cell(s) should be selected to express the antigen or antigen(s) of interest. A cell for use may have a limited or restricted specificity—i.e. it may express the antigen(s) of interest but lack other antigens of no interest.

red blood cells may have a 50% haematocrit tested by a validated analyser or specified in blood donation.

Ideally, cells should be <4 weeks old.

ÄKTA Purification

The ÄKTA Pure method queued three affinity purifications in sequence through two IgG Protein G HiTrap columns in positions 1, 2 and 3. The method included sequential equilibration and up-flow elution of the column. Samples were injected through the sample loop. Flow rate was lowered to 0.1 mL/min during sample loading.

TABLE 4

Inlet for affinity purification

| Inlet Pump | Buffer |
| --- | --- |
| A1 | Protein G Binding Buffer |
| A2 | Protein G Elution Buffer |
| A3 | Elix H$_2$O |

The Protein G column (column position 1, 2 and 3) was equilibrated with 5 mL ELIX H$_2$O, followed by 25 mL Protein G Binding Buffer before use. The general run method is shown in the Table 5.

TABLE 5

Protocol specifics for affinity purification

| Process Buffer Steps | Volume (mL) |
| --- | --- |
| Column equilibration (5 mL H$_2$O + 25 mL Binding Buffer) | 30 |
| Binding Buffer | 5 |
| Sample supernatant | 1 |
| Binding buffer | 20 |
| Elution buffer | 25 |
| Binding buffer | 5 |

Once the peak was detected, fractions were collected in 0.5 mL volumes into 96 deep well plates containing 50 µL of Neutralisation Buffer.

Buffer exchange was required immediately after purification due to the low pH of the elution buffer (0.1M Glycine pH 2-3); this was carried out using a Zeba desalting column. The peak fraction was identified through ÄKTA UV trace and total protein levels.

Acceptance Criteria

A constant flow rate of 1 ml/min$^{-1}$ and pressure <0.5 MPa was maintained throughout the affinity purification process.

The standard sampling loading/column washing/elution phases were clearly defined in the UV chromatogram of the AC process.

Concentration of Samples

Following affinity purification, the 1 mL IgG fractions from each specificity were pooled and concentrated by Ultracel centrifugal filters to a volume of 200 µL, ×5 concentrated (method as per IFU).

Fractions Printed Onto Array

TABLE 6

Concentration of probes printed onto antigen typing arrays.

| | | Starting Dilution (µL) | | | | Serial Dilution 50% |
| --- | --- | --- | --- | --- | --- | --- |
| Reagent | Probe Conc. (mg/mL) | Ab | PBS | Glyc | Stock | Glyc/PBS |
| Polyclonal Anti D | 1/2, 1/4, 1/8, 1/16, 1/32, 1/64 | 20 | 0 | 20 | 20 | 20 |
| Polyclonal Anti K | 1/2, 1/4, 1/8, 1/16, 1/32, 1/64 | 20 | 0 | 20 | 20 | 20 |
| Polyclonal Anti-Fy$^a$ | 1/2, 1/4, 1/8, 1/16, 1/32, 1/64 | 20 | 0 | 20 | 20 | 20 |
| ESD1 (anti-D) | 1/10, 1/20, 1/40, 1/80, 1/160, 1/320 | 10 | 40 | 50 | 50 | 50 |
| MS56 (anti-K) | 1/8, 1/16, 1/32, 1/64, 1/128, 1/256 | 12.5 | 37.5 | 50 | 50 | 50 |
| DG-FYA-02 (anti-Fy$^a$) | 1/2, 1/4, 1/8, 1/16, 1/32, 1/64 | 20 | 0 | 20 | 20 | 20 |

TABLE 6-continued

Concentration of probes printed onto antigen typing arrays.

|  |  | Starting Dilution (µL) | | | | Serial Dilution 50% |
| --- | --- | --- | --- | --- | --- | --- |
| Reagent | Probe Conc. (mg/mL) | Ab | PBS | Glyc | Stock | Glyc/PBS |
| Anti-Gylcophorin | 1/10, 1/20, 1/40, 1/80, 1/160, 1/320 | 10 | 40 | 50 | 50 | 50 |

Following affinity purification, the purified polyclonal antibodies were printed onto epoxysilane slides at the concentrations shown in Table 6. Anti-D (ESD1 V140550 B01), Anti-Fy$^a$ (DG-FYA-02, J25541 B01) and Anti-K (MS56 J25922 B01) were included as assay controls and to aid placement of grids for image analysis.

Slides were printed with the antibodies listed in Table 6 in a 16 mini array format. Each mini array consisted of a 12 by 12 rectangular grid. This was achieved by 8 source-plate visits with 4 drops per spot. In order to identify whether cross talk (between print-head nozzles) and carryover (between source plate visits) occurred during printing of the slides, 50% Glycerol/PBS was printed in alternate rows of the probe grid (FIGS. 1 and 2). A positive response in any of these probe sites would highlight print head malfunction or the printing of antibodies at too high a concentration. To limit carryover five printhead and Jetspyder purges and the incorporation of a wash plate (filled with Arrayjet buffer) were used. Slides were stored in a slide holder at 2-8° C. in the dark for 5 days prior to assay. FIGS. 1 and 2 show the source plate layout and resulting print layout (spot placement).

Acceptance Criteria:
Visual check of the slides and spots to check printing was successful.

Example Methods

An example method for the purification of polyclonal antibodies is provided in FIG. 6.
A further exemplary method according to this invention may be summarised as follows:
Prior to processing, donor red cells will be washed 3 times with 0.9% Saline (3500 RPM for 5 min, acc 9, dec 7.)
Plasma is incubated with red cells 70% haematocrit)at a ratio of 3:1 (Plasma:Cells) for 1 hour at 37° C. with gentle agitation every 15 mins.
The red cell/plasma solution is then centrifuged (3500 RPM for 5 min, acc 9, dec 7.) and the supernatant is removed without disruption of red cell pellet.
The supernatant volume is then replaced by saline solution.
The solution is then centrifuged (3500 RPM for 5 min, acc 9, dec 7.)
The wash protocol is repeated for a total of six rounds. Following the final wash, the supernatant is removed.
The packed cells are then mixed with elution buffer at a 2:1 ratio (elution buffer:cells) (Elution buffer=0.1M Glycine-HCl, pH 2.7+154 mM NaCl).
This mixture is then incubated at room temperature for 2 minutes.
Neutralisation buffer (1M Tris-HCl pH 9.0+154 mM NaCl) is then added representing 5% of the total volume of elution buffer to the cell mixture.
This solution is then mixed gently and centrifuged at 3500 RPM for 5 minutes (acc 9, dec 7).
The supernatant is then transferred to a clean container and the pH measured and any further adjustments made to make it pH 7.
The supernatant is diluted 1:1 in Protein G binding buffer.
The Protein G column is equilibrated with binding buffer.
The eluted antibody/binding buffer solution is injected onto the chromatography column at a low flow rate, while maintaining a constant pressure.
Following sample addition, the column is washed with 10 column volumes of binding buffer to wash-out the unbound antibody or contaminating proteins.
10 column volumes of Protein G elution buffer is then flushed through the column in an upward flowpath in order to elute the bound antibody.
The eluted antibody is then dialysed into PBS and concentrated.
The eluted antibody is collected for characterisation (gels and serology).
The concentrated antibody is then diluted in PBS+50% glycerol and printed to an epoxysilane surface. Binding is then investigated using the manual antigen typing assay and with positive and negative cells.

The invention claimed is:

1. A method of purifying an antibody with specificity for a certain or specific blood group antigen, said method comprising:
    subjecting a red blood cell or red blood cells to an antigen blocking or neutralising process or protocol prior to use, wherein the antigen blocking or neutralising process or protocol blocks or neutralises only those antigens which may bind antibodies which are not to be purified;
    contacting blood, a blood product, serum and/or plasma with the red blood cell or red blood cells under conditions which permit binding between unblocked/not neutralised blood group antigen(s) and antibody within the blood, blood product, serum and/or plasma; and
    isolating the bound antibody,
    wherein the method does not exploit cell membrane fragments or stroma.

2. The method of claim 1, wherein the method uses one or more red blood cells expressing one or more blood group antigens.

3. The method of claim 1, wherein the blood, blood product, plasma and/or serum is derived from or provided by a subject intending to donate blood (blood donors) and/or a subject immunised so as to produce antibodies to a specific target.

4. The method of claim 1, wherein the antibody is a polyclonal antibody.

5. The method of claim 1, wherein the red blood cell or red blood cells are not conjugated to a support, support substrate or polymer.

6. The method of claim 1 wherein the step of isolating the bound antibody involves dissociating and/or eluting antibodies absorbed or bound to the surfaces of the red blood cell(s).

7. The method of claim 6, wherein the dissociating and/or eluting procedures include the use of: heat, rapid freeze/thaw, ultrasonic baths, cell lysis, acid based elution/dissociation, cold acid, organic solvents, xylene, chloroform, modified heat/agitation or chloroquine diphosphate.

8. The method of claim 6, wherein the step of isolating the bound antibody involves contacting antibody/cell complexes with an elution buffer.

9. The method of claim 8, wherein the elution buffer is formulated to bring about antibody dissociation through acid elution.

10. The method of claim 8, wherein the elution buffer comprises, consists essentially of or consists of Glycine-HCl and NaCl.

11. The method of claim 1, wherein the antigen blocking or neutralising process or protocol uses antibodies as blocking or neutralising agents.

\* \* \* \* \*